(12) United States Patent
Brodkin

(10) Patent No.: US 7,338,523 B2
(45) Date of Patent: Mar. 4, 2008

(54) METHOD FOR ATTACHMENT OF ARTIFICIAL NAIL

(76) Inventor: Robert M. Brodkin, P.O. Box 5128, Lubbock, TX (US) 79408

( * ) Notice: Subject to any disclaimer, the term of this patent is extended or adjusted under 35 U.S.C. 154(b) by 210 days.

(21) Appl. No.: 11/163,873

(22) Filed: Nov. 2, 2005

(65) Prior Publication Data
US 2007/0100467 A1 May 3, 2007

(51) Int. Cl.
A61F 2/02 (2006.01)
(52) U.S. Cl. ...................... 623/11.11; 132/73
(58) Field of Classification Search ............ 623/11.11, 623/15.11, 15.12; 132/73
See application file for complete search history.

(56) References Cited

U.S. PATENT DOCUMENTS

| | | | |
|---|---|---|---|
| 3,487,831 A | 1/1970 | Jaume et al. | |
| 4,068,656 A | 1/1978 | Barmore | |
| 4,222,399 A | 9/1980 | Ionescu | |
| 4,361,160 A | 11/1982 | Bryce | |
| 4,445,234 A | 5/1984 | Ogunro | |
| 4,819,623 A * | 4/1989 | Ogunro | 602/22 |
| 5,060,678 A * | 10/1991 | Bauman et al. | 132/73 |
| 5,226,433 A | 7/1993 | Garcia-Carree | |
| 7,100,619 B2 * | 9/2006 | Kim | 132/73 |

* cited by examiner

*Primary Examiner*—Bruce E. Snow
(74) *Attorney, Agent, or Firm*—Michael L. Greenberg, Esq.; Greenberg & Lieberman, LLC

(57) ABSTRACT

A method for attaching an artificial nail. In patients who have a deformity of the fingernail or the toenail due to previous injuries, birth defects, or have undergone partial or entire matricectomies (wherein the root of the nail, which creates growth, is removed) due to severe cases of ingrown toenails, disclosed is a method of attachment of an artificial nail supported above the deformity by the use of three bone anchors, three posts, and a nail scaffold. A method for attaching an artificial nail that does not use adhesives, nor does it rely upon the patient having a natural nail to securely fit the artificial nail over the deformity.

4 Claims, 7 Drawing Sheets

METHOD FOR ATTACHMENT OF ARTIFICIAL NAIL

FIELD OF THE INVENTION

The present invention relates to a method for the aesthetic correction of a deformity of the toe or finger caused by a surgical operation for the correction of severe ingrown toenails, a birth defect, or an injury.

BACKGROUND OF THE INVENTION

In the field of foot surgery, when a patient is suffering from an ingrown toenail, doctors may perform a surgical operation referred to as "matricectomy," which involves the removal of part, or in serious cases the entirety of the nail root (also referred to as the "matrix"). The nail root is what causes the nail to renew cells and grow each day. If the nail root is partially or completely removed, there is either limited growth or no nail at all. If the patient has undergone a partial matricectomy, up to two-thirds of the toenail could be missing; in a full matricectomy, there would be no nail at all. The nail bed, which is normally where the nail would attach to the skin, would evolve into skin similar to the rest of the body. In a society that places much emphasis on physical appearance, this deformity may cause embarrassment to the patient from a cosmetic standpoint, for the toe and nail of a person who has suffered this deformity would look markedly different than one would expect.

Prior art has been designed to prevent, correct and/or treat ingrown toenails before or while they cause the surrounding skin to become inflamed and irritated, but these are generally preventative measures. Cosmetic, artificial nails, which cover damaged nails or serve as a prosthesis over the nail bed, are temporary in nature.

Prior art uses orthopedic structures or prosthetic nails as a method of separating the human nail from the skin in order to prevent ingrown nails. U.S. Pat. No. 4,086,656 issued to Barbara Barmore in 1973 describes a device that is placed under the nail to force the ingrown nail to grow upwards and out. U.S. Pat. No. 5,226,433, issued to Juan Garcia-Carree in 1993, discloses a device to correct an ingrown nail by inserting a thin piece of rigid material between the flesh and the problem nail.

The aforementioned patents are methods that are meant to simplify or to avoid the matricectomy necessary once an ingrown toenail has become painful. Unfortunately, these structures do not account for the necessity of aesthetic correction of the deformity after the surgical correction.

Previous designs have disclosed artificial nails, which are glued on directly to the human nail to generally enhance or elongate the nail (primarily for aesthetic purposes in women). For example, U.S. Pat. No. 3,487,831, issued to Jaume et al. in 1970, describes an artificial nail with a pocket that fits over the edge of the human nail and is glued on at the base. U.S. Pat. No. 4,222,399, issued to Miruleta Ionescu in 1980, shows a similar device that uses liquid nail glue to attach the nail. Thomas Bryce's U.S. Pat. No. 4,361,160 (issued in 1982) demonstrates a method of forming artificial nails through plaster molds of the finger.

These nails depend upon the user's natural nails to adhere to the digit and perform the method correctly. The consensus among matricectomy patients is that these nails have a tendency to be ineffective for their purposes, due in part to the nails coming off on their own at inconvenient times, such as when the patient is wearing sandals or is at the beach. The resulting embarrassment in the matricectomy patient is due to the deformed nail being in plain view to other people.

Some previous inventions have designed artificial nails for a more functional purpose wherein the artificial section will adhere over a partial nail or nail bed in an attempt to conceal the problem. U.S. Pat. No. 4,445,234 issued to Olayinka Ogunro in 1984, is a mechanism by which an artificial nail is implanted into the nail bed. U.S. Pat. No. 5,060,678 issued to Bauman et al. in 1991 describes an artificial acrylic nail surgically implanted into the bed by means of three anchors, and the nail is permanently placed into the nail bed. However these structures are put in place permanently and the patient cannot remove the nail at will.

Hence, there is a need for a method of attaching an artificial nail that a) completely covers the deformity of a partial or missing fingernail or toenail due to a matricectomy or other causes; b) does not use adhesives, glues or cements, but provides a more secure fit than the artificial nails that do; c) does not necessitate that the user have an intact natural nail; d) leaves room between the nail bed and artificial nail for hygienic purposes; and e) is able to come off if the user so desires but will not fall off on its own.

SUMMARY OF THE INVENTION

It is an object of the present invention to provide for a method that implements an artificial nail for people who have suffered from: ingrown toenails and the subsequent matricectomies, which partially or completely remove the nail; injuries to the finger or toenails due to accidents; and birth defects to the finger or toenails. The present invention provides a patient with the option of wearing a secure, discreet prosthetic nail over a damaged nail bed that can be removed by the patient at will, but cannot be detached or displaced on its own. It is an underlying motivation of the present invention to eliminate the embarrassment in patients caused by adhesive artificial nails falling off and exposing the deformity of the nail.

Unlike previous inventions where an artificial nail would be attached to the natural nail by the use of an adhesive, the present invention does not necessitate that the user even have a natural nail. Prior art depends upon the natural nail to adhere to the artificial nail, but the present invention attaches the artificial nail to the human digit through the bone of the toe, in this way avoiding the use of glues, adhesives or cements. The present invention does not attach the artificial nail directly to the natural nail, but rather supports the nail slightly above the nail bed, thereby facilitating cleansing and reducing the chances of debris accumulating between the nail bed and the artificial nail.

The present method is explained in greater detail in the detailed description. The average size of the distal phalanx of the great toe in an adult is ¾" in width at the base, about ½" in width at the narrow waist segment, and about 1" in length. The distal phalanx is the normal point of attachment of both the nail bed and the nail plate in all fingers and toes. On larger bones, it is standard practice to set any internal fixation device freehand; however, because the distal phalanx is such a small bone, there is less margin for error. An internal fixation device for the nail includes a pin, wire, screw, plate and other hardware meant to stay in place either short or long term. If a hole is incorrectly drilled for the placement of a bone screw, it would be nearly impossible to go back and drill it correctly.

Therefore, the relatively large size of the pin guide of the present invention allows for greater precision using the "line of sight" method for alignment of the bone anchors and the scaffold. The line of sight method allows for far greater precision than would be possible using just the end of the toe or finger as a point of reference. The pin guide measures preferably 5" in length and 5" at its maximum width. One of the purposes of the pin guide is to allow accurate placement of the three skin incisions needed for the procedure. The extra length of the pin guide relative to the small size of the distal phalanx provides greater accuracy of the longitudinal placement, while the extra width increases the accuracy of the transverse placement. The tubules of the pin guide hold the pin in the correct alignment and angle, and will control or eliminate the tendency of the tip of the drill bit or wire to walk along the surface. The rigidity of the pin guide will assure that the pins and screws are correctly angled, time after time. Other freehand surgical techniques or methods would not provide for this level of precision and accuracy.

BRIEF DESCRIPTION OF THE DRAWINGS

FIG. 2 is the present embodiment complete with the nail scaffold, without the artificial nail clipped on.

FIG. 3 is the distal phalanx with the initial guide wire centrally placed at the base of the bone, and the three points are where the incisions are made into the skin.

FIG. 4 shows the pin guide, which is diamond shaped, and how it is placed over the guide wire to assure that the incisions for the bone anchors are evenly spaced and accurately placed.

FIG. 5 portrays the distal phalanx once the bone anchors have been set.

FIG. 6 shows the bone anchors set in place.

FIG. 7 shows the nail scaffold.

DETAILED DESCRIPTION OF THE PREFERRED EMBODIMENTS

Figure 1:
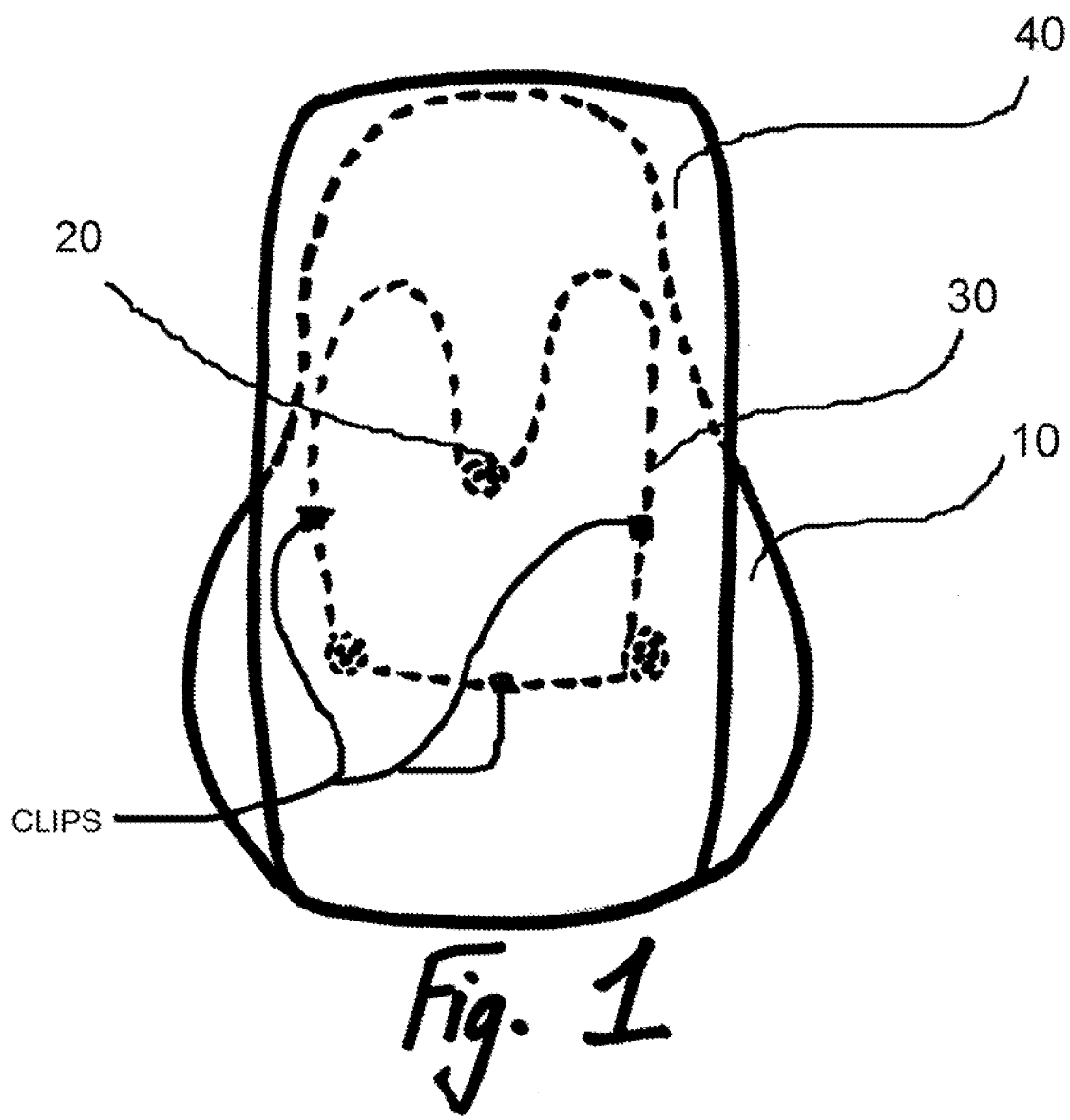
FIG. 1 is the present embodiment in its completed state. The artificial nail is clasped onto the nail scaffold.
Figure 2:
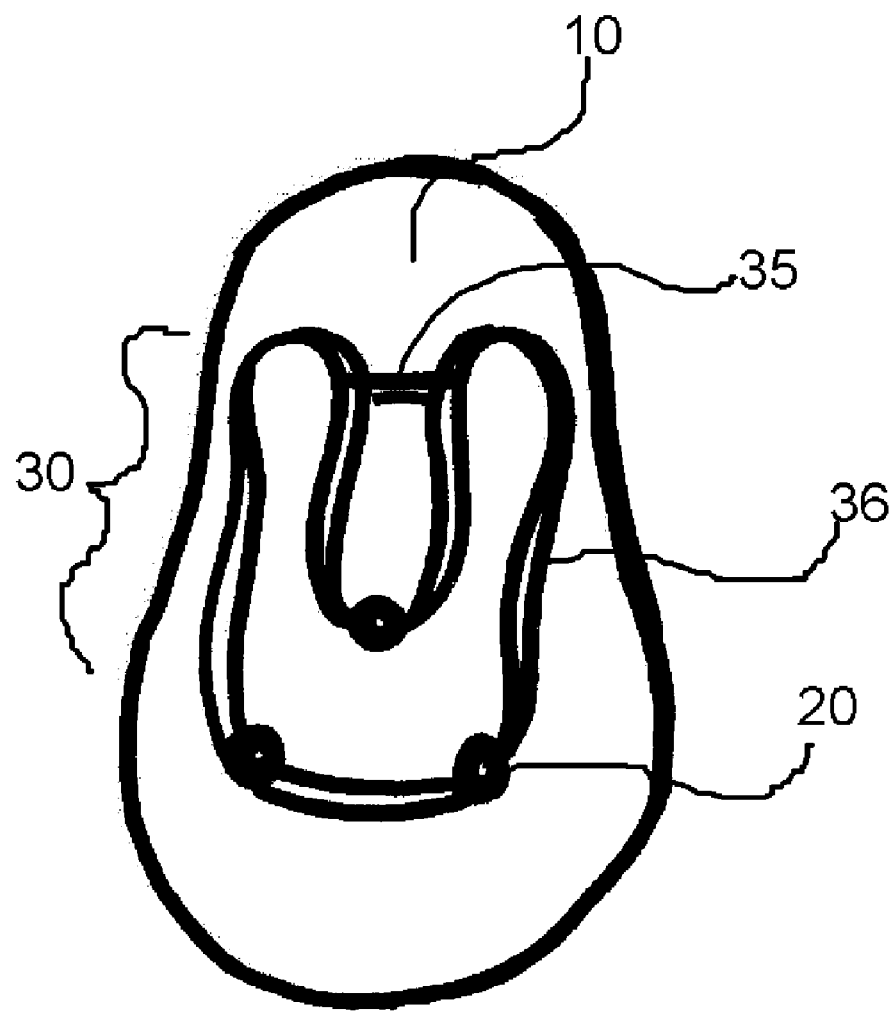
Figure 3:
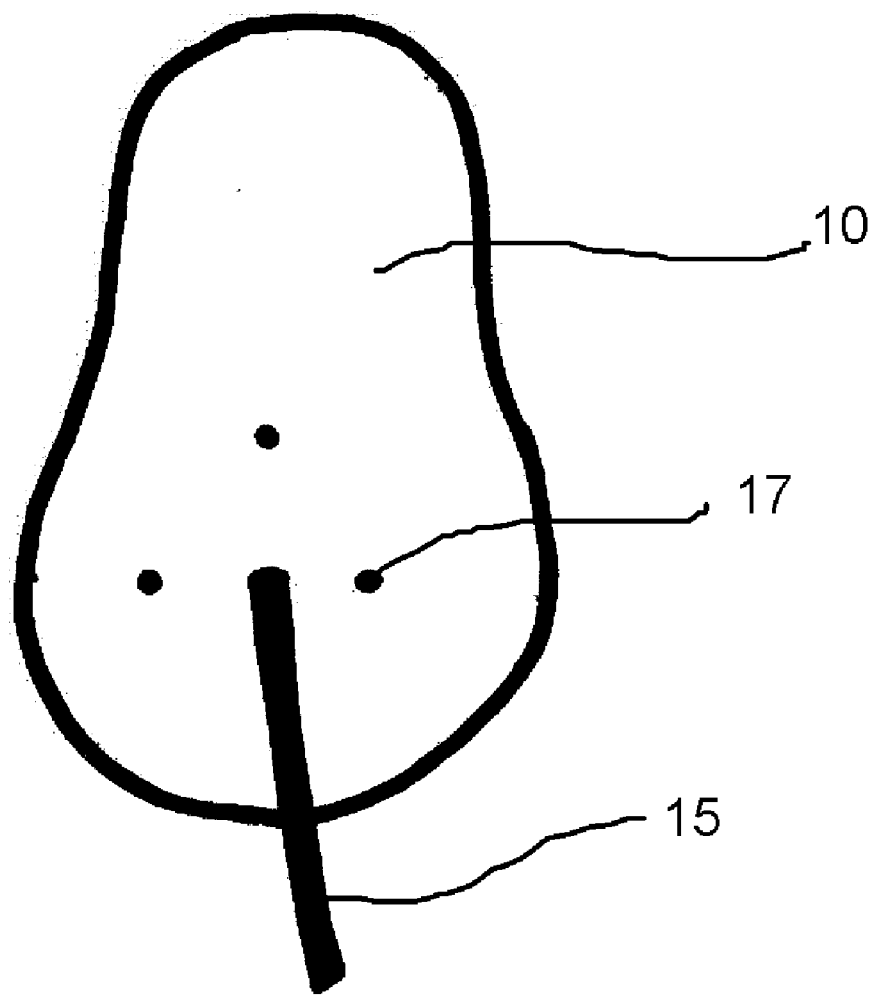
FIGS. 3-7 disclose the methodology of implementing the apparatus.

The overall method of the present invention attaches, by means of a threaded post 32, a "scaffold" 30 into the bone of the toe 10 (distal phalanx) with bone anchors 20, and the artificial nail 40 is attached to the scaffold 30 by a positive clip-type action. Please refer to FIG. 1 and FIG. 2 to see the completed result of the method.

Figure 4:
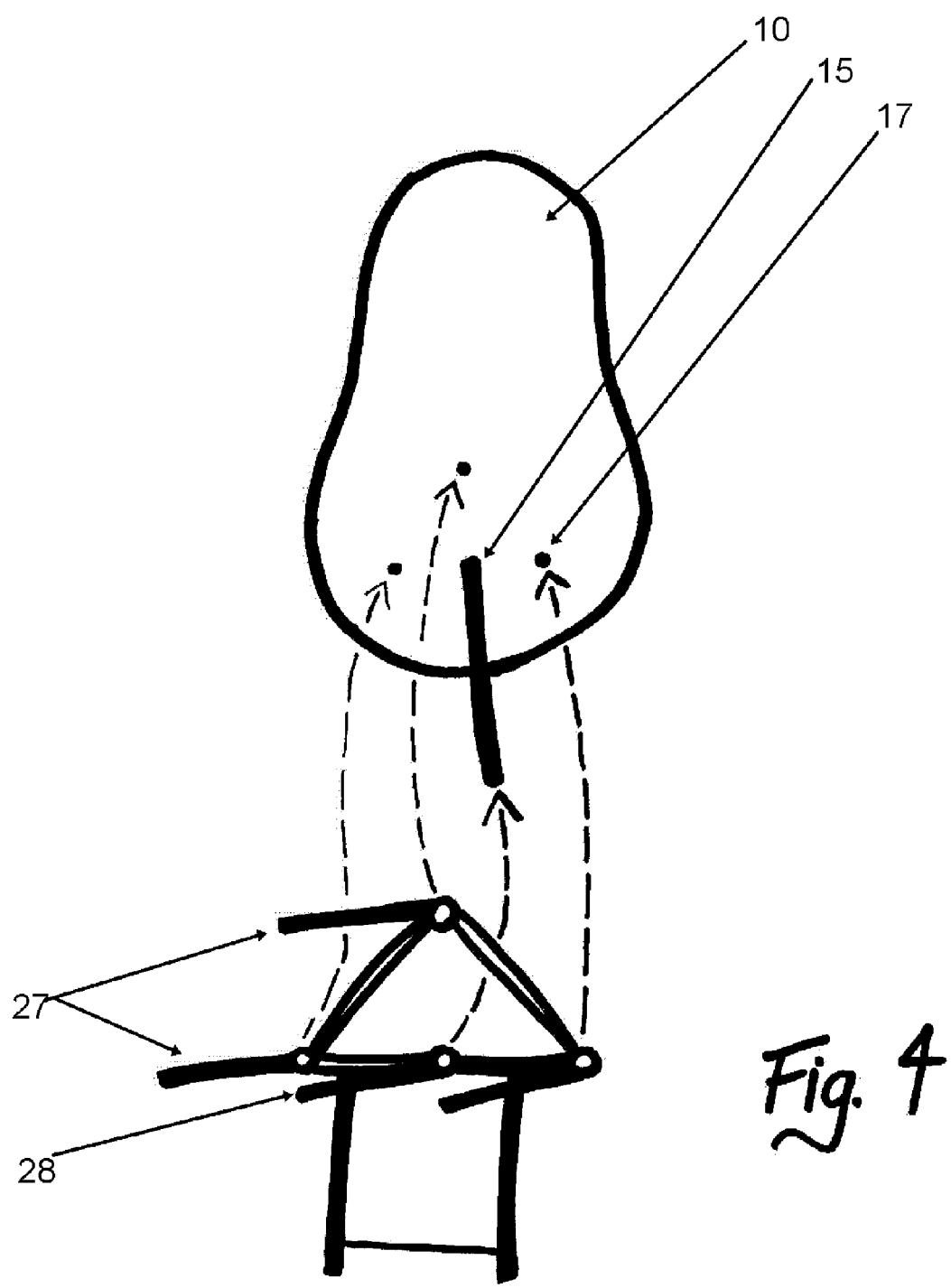
Figure 5:
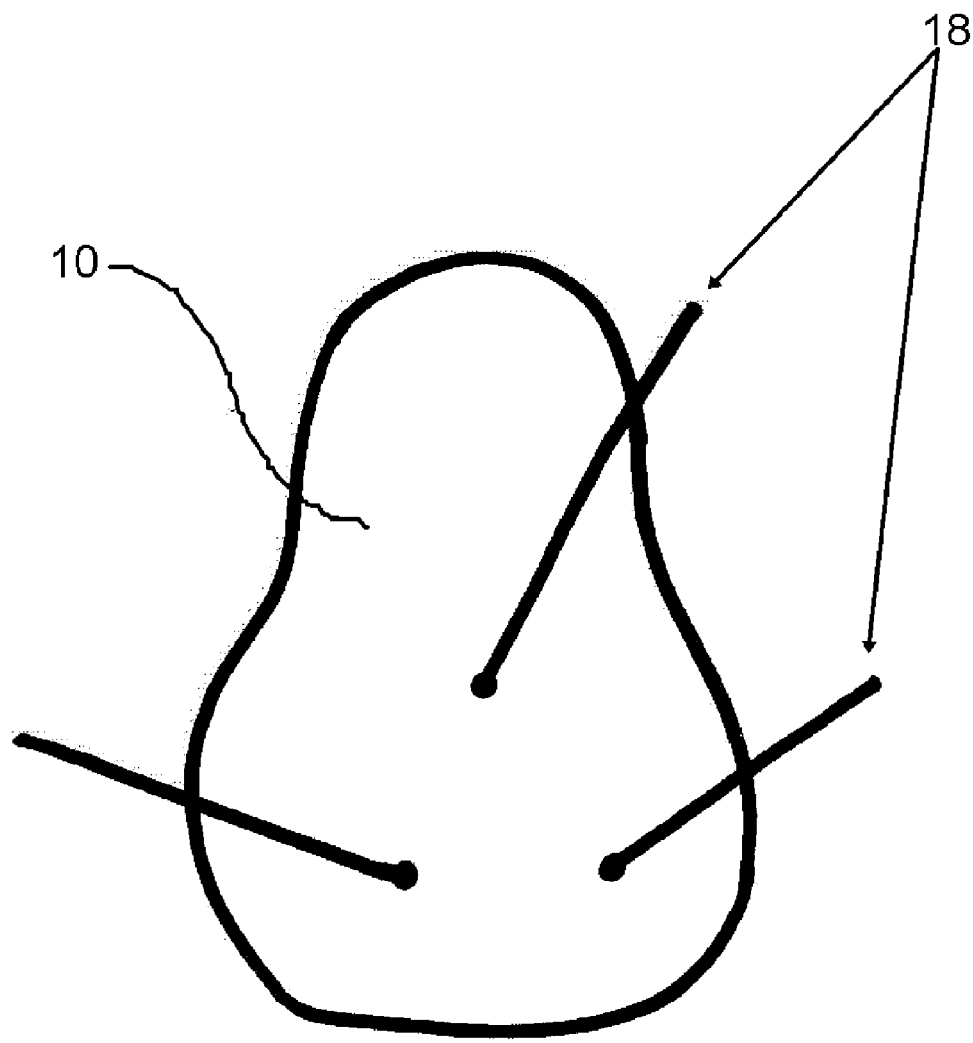

The first step of the method is to implement a guide wire 15 of 0.035" in diameter, which is centrally placed through the distal phalanx 10. In FIG. 4, a pin-guide device 27 with four tubules 28 slightly larger than the guide wire 15, arranged in a diamond fashion with relatively long metal extensions 27, and the use of Velcro, allows the surgeon to make three tiny incisions 17 (to align the pins 18 and subsequently bone screws 20 correctly with the center of the distal phalanx 10 as shown in FIG. 5). The back tubule 28 of the pin-guide 27 fits over the guide wire 15 that was previously inserted into the bone 10.

The pin guide 27 helps to mark the location of three tiny incisions of the dorsal aspect of the distal phalanx 10. The pin guide 27 eliminates walking of the drill when the bone screws 20 are inserted; avoids damage to any skin still in place on the distal phalanx 10; and assures the drill holes/incisions 17 will be symmetrical, evenly placed and line up exactly with the nail scaffold 30. In this way, the doctor accurately inserts the bone screws 20, so the patient's artificial toenail is not off-center or crooked. The skin is then gently freed to allow placement of the bone screws.

Figure 6:
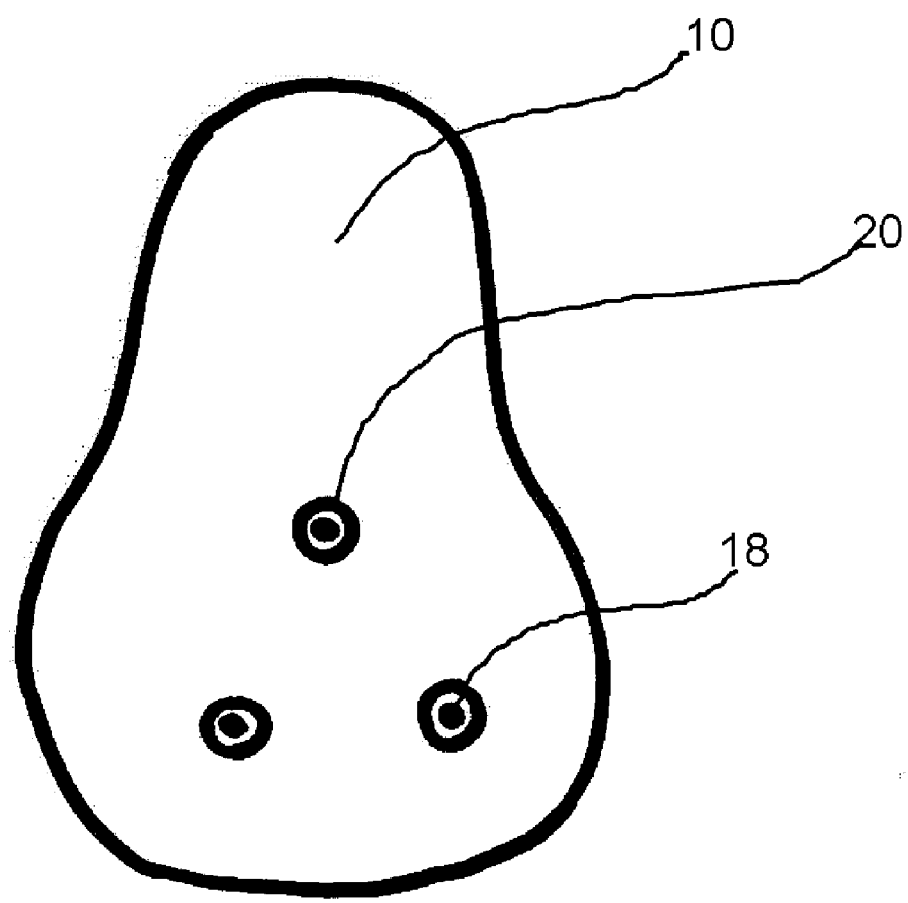

The guide pins 18 must be checked for alignment and accuracy, and then the cannulated bone screws 20 are run directly over the guide wires 18, as shown in FIG. 6. The heads of the bone screws 20 (sometimes referred to as "anchors") are preferably made of titanium and sit flush with the surface of the bone. There is a dissection of the medial and lateral skin flaps where previous tiny incisions 17 were made as marked using the pin guide 27.

Therefore, the three anchors 20 are completely embedded within the bone 10. Scar tissue surrounds the threaded posts, which run from inside the cannulated bone screws and up through the skin and limits the passage of bacteria. The fact that the posts are threaded as opposed to smooth is meant to provide a greater surface area for scar tissue to adhere to. Each bone anchor 20 is "cannulated," meaning a hole is drilled directly in the center of the screw. The screws are cannulated to a) allow for the screw to be guided to a very precise placement; b) serve as the placement of another 0.045" threaded post. The cementing of the threaded posts is done with FDA-approved bone cement. Therefore, there are three permanent supporting posts 32 for the nail scaffold 30, supported by the three respective posts 32. It is therefore imperative that the bone anchors 20 match up exactly with the posts 32 of the nail scaffold 30. There must be three bone anchors 20 arranged in a triangular fashion so that the artificial nail 40 is stable. Preferably there is one anchor 20 on the distal end and two on the opposite end, as there is more room to work with two anchors 20 at the base of the distal phalanx 10.

Figure 7:
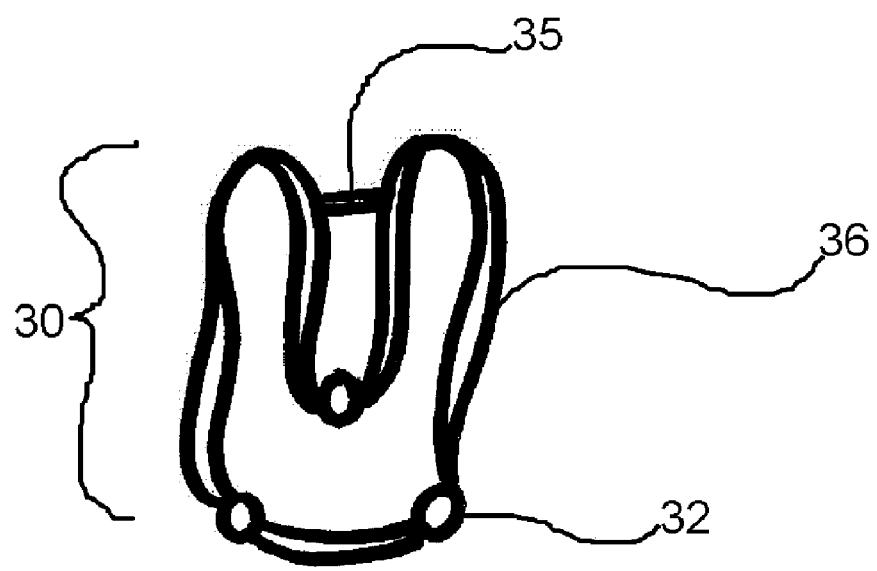

As shown in FIG. 7, the scaffold 30 is made of stainless steel wire, with three short spacer tubules 32 that attach to the threaded posts 20 cemented inside the patient's toe. The nail scaffold is not available on the current market but would be provided to the surgeon as a part of the nail bed implant system. The scaffold 30 will tend to be rectangular in shape to give as much support as possible to the nail 40. As a part of the manufacturing process, the plastic clips will be attached to a marked, factory-use scaffold. Then, the clips are glued to the underside of the nail in the correct position. When the adhesive sets, the nail can be unclipped.

There are a certain number of standard-sized nail scaffolds built around a wire-forming jig at the factory. The system includes several scaffolds of different sizes. If the surgeon installs a #2 scaffold, the standardization assures that a #2 nail will fit properly. Nail re-orders by the patient will be based on the size of the scaffold put in place during surgery, as the surgeon uses his/her judgment to fit a scaffold that best fits the shape of the toe. All scaffolds, regardless of size, will have three spacers attached in exactly the same pattern of the pin guide. Some scaffolds will therefore have a wire-forming jig to indent a side for attachment of the spacer. The spacers may be attached during manufacturing, but it is anticipated that the high temperature of 2,500 degrees Fahrenheit needed for welding would adversely affect the springiness of the metal. A preferred method of attachment is via a two-part bonding system with a strength greater than 3,000 pounds per square inch.

A 1 mm wire 35 is passed underneath the scaffold 30 when it is put in place to act as a "spacer" in between the flesh of the nail bed and the scaffold 30. The spacer 35 avoids placing the artificial nail 40 in direct contact with the skin of the nail, which reduces the likelihood of infection, facilitates cleansing of that area, and enables free passage of air between the nail 40 and skin. Moreover, the spacer 35 allows the clasps of the clip-on artificial nail 40 to attach to the wires 36 on the nail scaffold 30. Hence it is crucial that the scaffold 30 is placed correctly on the bone 10. Once the cement has set the posts 32 in place, the spacers 35 are removed, allowing the scaffold 30 to be permanently suspended above the skin.

Once the bone has healed well, expected to be sometime after the twenty-first day post-operatively, the artificial nails 40 are then clipped onto the nail scaffold 30. Almost any plastic can be used to form the nails, and airbrushed color can be applied during manufacturing so that the scaffold does not show through the nail. It is possible that a laser device can be used during the manufacture of the nails to create micro-pores. These would be invisible to the casual observer, but would allow the passage of both air and water, allowing the skin underneath to maintain normal quality and allowing for faster drying of the skin after bathing. The nails have a mechanism of attachment that can be varied per the user. They utilize a numerical scale from 1 to 5, with 1 being the easiest to remove and 5 providing the strongest, sturdiest fit and being the most difficult to remove. The user can re-order the nails depending on the strength of the clip-on action that suits them best. The plastic clips are bonded to the underside of the nails, and the nails are then clipped on to the nail scaffold. Therefore, the artificial nail is supported over the damaged/missing nail through the bone of the patient, obviating the need for a natural nail.

The underside of the artificial nails is not completely smooth, but has two ridges running from right to left. Each raised surface has a slit into which the wire of the scaffold would fit, and a perfectly round, molded insert to hold the wire 35 of the scaffold 30 firmly in place.

Having illustrated the present invention, it should be understood that various adjustments and versions might be implemented without venturing away from the essence of the present invention. The present invention is not limited to the embodiments described above, and should be interpreted as any and all embodiments within the scope of the following claims.

What is claimed is:

1. A method for attachment of an artificial nail to a nail bed for a patient, comprising:
    placing a guide wire above the nail bed of the distal phalanx of the patient;
    placing a pin-guide device in communication with said guide wire;
    placing guide pins through said pin-guide device;
    placing bone anchors in communication with said guide pins;
    placing threaded posts in communication with said bone anchors; and
    placing a nail scaffold in communication with said threaded posts; and
    placing an artificial nail in communication with said nail scaffold.

2. The method of claim 1 wherein said artificial nail is removable from said nail scaffold.

3. The method of claim 1 wherein said pin-guide device is larger than the size of the distal phalanx.

4. The method of claim 1 wherein said artificial nail is placed over a damaged or missing nail of said patient on said nail scaffold and held through said distal phalanx of the patient.

* * * * *